United States Patent
Bauer et al.

(10) Patent No.: US 9,738,858 B2
(45) Date of Patent: Aug. 22, 2017

(54) MIXTURES OF COMPOUNDS, THEIR PREPARATION, AND USES

(71) Applicant: BASF SE, Ludwigshafen (DE)

(72) Inventors: Frederic Bauer, Deidesheim (DE); Rainer Eskuchen, Langenfeld (DE); Juergen Tropsch, Roemerberg (DE)

(73) Assignee: BASF SE, Ludwigshafen (DE)

( * ) Notice: Subject to any disclaimer, the term of this patent is extended or adjusted under 35 U.S.C. 154(b) by 51 days.

(21) Appl. No.: 14/901,850

(22) PCT Filed: Jun. 26, 2014

(86) PCT No.: PCT/EP2014/063551
§ 371 (c)(1),
(2) Date: Dec. 29, 2015

(87) PCT Pub. No.: WO2015/000792
PCT Pub. Date: Jan. 8, 2015

(65) Prior Publication Data
US 2016/0312154 A1  Oct. 27, 2016

(30) Foreign Application Priority Data
Jul. 3, 2013 (EP) .................................... 13174915

(51) Int. Cl.
| | | |
|---|---|---|
| C11D 1/825 | (2006.01) | |
| C11D 3/22 | (2006.01) | |
| C07H 1/00 | (2006.01) | |
| C07H 3/02 | (2006.01) | |
| C07H 3/04 | (2006.01) | |
| C07H 3/06 | (2006.01) | |
| B08B 3/04 | (2006.01) | |
| C07H 15/04 | (2006.01) | |
| C11D 1/66 | (2006.01) | |
| C11D 3/20 | (2006.01) | |
| C07C 31/125 | (2006.01) | |

(52) U.S. Cl.
CPC ............ *C11D 3/225* (2013.01); *C07C 31/125* (2013.01); *C07H 15/04* (2013.01); *C11D 1/662* (2013.01); *C11D 3/2017* (2013.01)

(58) Field of Classification Search
CPC ..... C11D 1/825; C11D 3/2006; C11D 3/2017; C11D 3/22; C07H 1/00; C07H 3/02; C07H 3/04; C07H 3/06; B08B 3/04
See application file for complete search history.

(56) References Cited

U.S. PATENT DOCUMENTS

| 5,681,949 A | 10/1997 | Johansson et al. |
|---|---|---|
| 5,928,993 A | 7/1999 | Johansson et al. |
| 2003/0181347 A1* | 9/2003 | Johansson ............... A61K 8/068 510/417 |
| 2012/0245070 A1 | 9/2012 | Eskuchen et al. |
| 2013/0303430 A1 | 11/2013 | Reinoso Garcia et al. |
| 2015/0368588 A1 | 12/2015 | Bauer et al. |
| 2016/0010027 A1 | 1/2016 | Bauer et al. |

FOREIGN PATENT DOCUMENTS

| EP | 2 336 280 A1 | 6/2011 |
|---|---|---|
| WO | WO 94/21655 A1 | 9/1994 |
| WO | WO 96/34078 A1 | 10/1996 |

OTHER PUBLICATIONS

International Search Report and Written Opinion issued Aug. 1, 2014 in PCT/EP2014/063551.

\* cited by examiner

*Primary Examiner* — Brian P Mruk
(74) *Attorney, Agent, or Firm* — Oblon, McClelland, Maier & Neustadt, L.L.P.

(57) ABSTRACT

The current invention is directed towards mixtures of compounds, comprising (A) in the range of from 93 to 97% by weight compound of general formula (I) (B) in the range of from 3 to 6.5% by weight compound of general formula (II) (C) in the range of from 0.2 to 0.5% by weight compound of general formula (III) wherein the integers are defined as follows: $R^1$ is $—(CH_2)_nCH_3$, $R^2$ is $—(CH_2)_{n+2}CH_3$, $R^3$ is $—(CH_2)_{n+1}CH(CH_3)_2$, $R^4$ is $—(CH_2)_{n-1}CH(CH_3)_2$ $G^1$ selected from monosaccharides with 4 to 6 carbon atoms, x in the range of from 1.1 to 10, n is a number in the range of from 1 to 4.

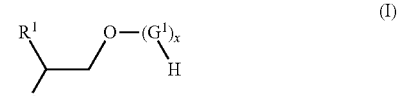

(I)

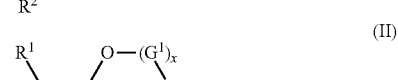

(II)

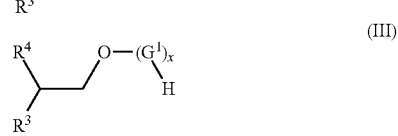

(III)

12 Claims, No Drawings

MIXTURES OF COMPOUNDS, THEIR PREPARATION, AND USES

Mixtures of compounds, their preparation, and uses

The current invention is directed towards mixtures of compounds, comprising (A) in the range of from 93 to 97% by weight compound of general formula (I),

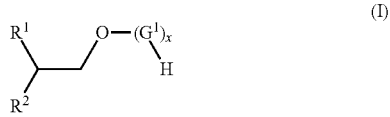

(B) in the range of from 3 to 6.5% by weight compound of general formula (II),

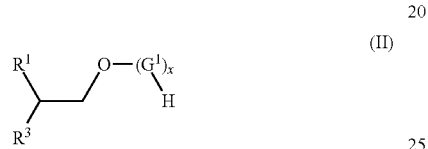

(C) and in the range of from 0.1 to 0.5% by weight compound of general formula (III)

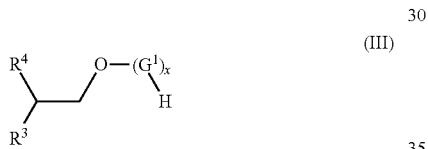

wherein the integers are defined as follows:
$R^1$ is —$(CH_2)_n CH_3$,
$R^2$ is —$(CH_2)_{n+2} CH_3$,
$R^3$ is —$(CH_2)_{n+1} CH(CH_3)_2$,
$R^4$ is —$(CH_2)_{n-1} CH(CH_3)_2$
$G^1$ is selected from monosaccharides with 4 to 6 carbon atoms,
x in the range of from 1.1 to 10,
n is a number in the range of from 1 to 4.

Furthermore, the present invention is directed towards the use of mixtures of compounds according to the invention, and to a process for making the mixtures according to the invention. Additionally, the present invention is directed towards mixtures and aqueous formulations containing at least one mixture according to the invention.

When cleaning surfaces such as hard surfaces or fibers with aqueous formulations several problems have to be solved. One task is to solubilize the dirt that is supposed to be removed and to keep it in the aqueous medium. Another task is to allow the aqueous medium to come into contact with the surface to be cleaned. A particular purpose of such hard surface cleaning can be degreasing. Degreasing as used in the context with the present invention refers to the removal of solid and/or liquid hydrophobic material(s) from a respective surface. Such solid or liquid hydrophobic material may contain additional undesired substances such as pigments and in particular black pigment(s) such as soot.

Some alkyl polyglucosides ("APG") such as described in WO 94/21655 are well known for degreasing lacquered or non-lacquered metal surfaces. When trying to apply 2-n-propylheptyl glucoside to laundry, however, it has turned out that the wetting behaviour was only unsatisfactory. In addition, the foaming behaviour still can be improved since many of them develop a lot of foam quickly on occasion of agitation.

It was therefore an objective of the present invention to provide a surfactant that exhibits excellent wetting and foaming behaviour. It was further an objective to provide a method for making a surfactant that exhibits an excellent wetting and foaming behaviour. It was further an objective to provide a method of use of surfactants that apply excellent wetting and foaming behaviour.

Accordingly, the mixtures of compounds defined in the outset have been found, them being also referred to as mixtures according to the invention or mixtures of compounds according to the invention.

Mixtures according to the invention comprise (A) in the range of from 93 to 97% by weight compound of general formula (I),

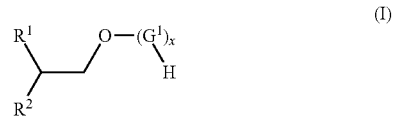

(B) in the range of from 3 to 6.5% by weight compound of general formula (II),

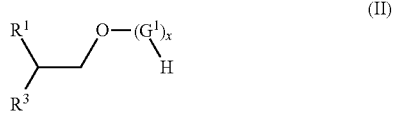

(C) and in the range of from 0.1 to 0.5% by weight compound of general formula (III)

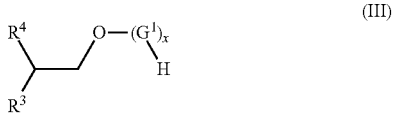

wherein the integers are defined as follows:
$R^1$ is —$(CH_2)_n CH_3$,
$R^2$ is —$(CH_2)_{n+2} CH_3$,
$R^3$ is —$(CH_2)_{n+1} CH(CH_3)_2$,
$R^4$ is —$(CH_2)_{n-1} CH(CH_3)_2$
$G^1$ selected from monosaccharides with 4 to 6 carbon atoms,
x different or preferably identical and in the range of from 1.1 to 10, preferred are 1.1 to 4, more preferred are 1.1 to 2 and in particularly preferred are 1.15 to 1.8. In the context of the present invention, x refers to average values, and x is not necessarily a whole number. In a specific molecule only whole groups of $G^1$ can occur. It is preferred to determine x by High Temperature Gas Chromatography (HTLC).
n is a number in the range of from 1 to 4, preferred is 1 or 2, and particularly preferred is 2.
$G^1$ selected from monosaccharides with 4 to 6 carbon atoms, for example tetroses, pentoses, and hexoses. Examples of tetroses are erythrose, threose, and erythulose. Examples of pentoses are ribulose, xylulose, ribose, arabinose, xylose and lyxose. Examples of hexoses are galactose, mannose and glucose. Monosaccharides may be synthetic or derived or isolated from natural products, hereinafter in brief referred to as natural saccharides or natural polysaccharides, and natural saccharides natural polysaccharides being preferred. More preferred are the following natural monosaccharides: galactose, arabinose, xylose, and mixtures of the foregoing, even more preferred are glucose, arabinose and xylose, and in particular glucose. Monosaccharides can be selected from any of their enantiomers, naturally occurring enantiomers and naturally occurring mixtures of enantiomers being preferred.

In one embodiment of the present invention, $G^1$ is selected from monosaccharides, preferably from glucose.

As indicated above, x can be preferably determined by high temperature gas chromatography (HTGC), e.g. 400° C., in accordance with K. Hill et al., Alkyl Polyglycosides, VCH Weinheim, New York, Basel, Cambrigde, Tokyo, 1997, in particular pages 28 ff.

In each specific mixture according to the invention, the respective integer n is identical for the respective compound of general formula (I) and the respective compound of formula (II) and for the respective compound of formula (III).

In each specific mixture according to the invention, the respective integer $G^1$ is identical for the respective compound of general formula (I) and the respective compound of formula (II) and for the respective compound of formula (III).

In single molecules of formulae (I), (II) and (III) with 2 or more monosaccharide groups, the glycosidic bonds between the monosaccharide units may differ in the anomeric configuration (α-; β-) and/or in the position of the linkage, for example in 1,2-position or in 1,3-position and preferably in 1,6-position or 1,4-position.

The integer x is a number in the range of from 1.1 to 4, preferred are 1.1 to 2 and in particularly preferred are 1.15 to 1.9. As stated before, in the context of the present invention, x refers to average values, and they are not necessarily whole numbers. Naturally, in a specific molecule of formulae (I), (II) or (III) only whole groups of $G^1$ can occur.

In specific molecules of formulae (I), (II) and (III), there may be, for example, only one $G^1$ moiety or up to 15 $G^1$ moieties per molecule.

Alkyl polyglycosides such as compound of general formulae (I), (II) and (III) are usually mixtures of various compounds that have a different degree of polymerization of the respective saccharide. It is to be understood that in formulae (I), (II) and (III), x is a number average value, preferably calculated based on the saccharide distribution determined by high temperature gas chromatography (HTGC), e.g. 400° C., in accordance with K. Hill et al., Alkyl Polyglycosides, VCH Weinheim, New York, Basel, Cambrigde, Tokyo, 1997, in particular pages 28 ff., or by HPLC. If the values obtained by HPLC and HTGC are different, preference is given to the values based on HTGC.

In a particularly preferred embodiment of the present invention, in mixtures according to the invention the integers are selected as follows: n is zero, x being in the range of from 1.15 to 2, and $G^1$ is glucose.

In one embodiment of the present invention, mixtures according to the invention can have a Hazen colour number in the range of from 10 to 1,000, preferably in the range of from 50 to 800 and more preferably in the range of from 100 to 500.

The Hazen colour number can be determined according to DIN EN ISO 6271-1 or 6271-2.

In one embodiment of the present invention, mixtures according to the invention can have a Gardner colour number in the range of from 0.1 to 8.0, preferably in the range of from 0.5 to 5.0 and more preferably in the range of from 1.0 to 3.5.

The Gardner colour number can be determined according to DIN EN ISO 4630-1 or 4630-2.

Both Hazen and Gardner numbers are determined based on 10% solutions.

Mixtures according to the invention are very good surfactants and particularly useful for hard surface cleaning. In particular, they solve the problems mentioned above.

In one embodiment of the present invention, mixtures according to the invention may contain at least one mixture according to any of the preceding claims and at least one further isomer of either compound (I), compound (II) or compound (III), such isomer being different from each of compounds according to general formulae (I), compound (II) and compound (III). Such isomers are preferably different with respect to the branching of the respective alkyl group.

Another aspect of the present invention are compositions comprising at least one mixture according to the invention and at least one further surfactant that is not covered by either of formulae (I) to (III), preferably at least one non-ionic surfactant that is not covered by either of formulae (I) to (III). Particularly preferred are alkyl polyglycosides based on linear fatty alcohols, for example alkyl polyglycosides based on linear $C_8$-$C_{14}$-alkanols.

Isomers preferably refer to compounds in which the sugar part is identical to $G^1$ in the particular compound but the alkyl group being different.

In one embodiment of the present invention, mixtures according to the invention comprise in the range of from 90 to 98% by of compound of general formula (I); preferably 93 to 97% by weight,
1.9 to 9.5% by weight of compound of general formula (II), preferably 3.7 to 6.7% by weight,
0.1 to 0.5% by of compound of general formula (III), preferably up to 0.3% by weight.

The amounts are preferably determined by gas chromatography or by NMR methods, e. g., by 2-dimensional NMR spectroscopy.

Mixtures according to the invention are extremely useful for cleaning hard surfaces, and in particular for degreasing metal surfaces. If applied as aqueous formulations, they exhibit a long shelf life.

A further aspect of the present invention is a process for making the mixture according to the present invention, hereinafter also defined as synthesis according to the invention. The synthesis according to the invention comprises the step of reacting a mixture of alcohols of the general formulae (IV), (V) and (VI)

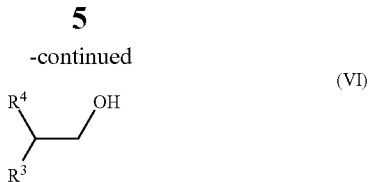

(VI)

with a monosaccharide, disaccharide or polysaccharide containing a $G^1$ group in the presence of a catalyst.

In alcohols of the general formulae (IV), (V) and (VI), the moieties $R^1$ to $R^4$ are defined as above in the respective mixture according to the invention.

In one embodiment of the present invention, the synthesis according to the invention is being carried out using a monosaccharide, disaccharide or polysaccharide or mixture of at least two of monosaccharides, disaccharides and polysaccharides as starting material. For example, in cases in which $G^1$ is glucose, glucose syrup or mixtures from glucose syrup with starch or cellulose can be used as starting material. Polymeric glucose usually requires depolymerisation before conversion with alcohol of general formulae (IV), (V) and (VI), respectively. It is preferred, though, to use either a monosaccharide or a disaccharide or a polysaccharide of $G^1$ as starting material.

In one embodiment of the synthesis according to the invention, alcohol of the general formulae (IV), (V) and (VI), and monosaccharide, disaccharide or polysaccharide are selected in a molar ratio in the range of from 1.5 to 10 mol alcohol per mol monosaccharide, disaccharide or polysaccharide, preferred 2.3 to 6 mol alcohol per mol monosaccharide, disaccharide or polysaccharide, the moles of monosaccharide, disaccharide or polysaccharide being calculated on the base of the respective $G^1$ groups.

Catalysts may be selected from acidic catalysts. Preferred acidic catalysts are selected from strong mineral acids, in particular sulphuric acid, or organic acids such as sulfosuccinic acid or aryl sulfonic acids such as para-toluene sulfonic acid. Other examples of acidic acids are acidic ion exchange resins. Preferably, an amount in the range of from 0.0005 to 0.02 mol catalyst is used per mole of sugar.

In one embodiment, the synthesis according to the invention is being performed at a temperature in the range of from 90 to 125° C., preferably from 100 to 115° C., particularly preferred from 102 to 110° C. In embodiments where G is selected to be xylose, the synthesis according to the invention is being performed at a temperature in the range of from 95 to 100° C.

In one embodiment of the present invention, the synthesis according to the invention is carried over a period of time in the range of from 2 to 15 hours.

During performing the synthesis according to the invention, it is preferred to remove the water formed during the reaction, for example by distilling off water.

In one embodiment, the synthesis according to the invention is being carried out at a pressure in the range of from 20 mbar up to normal pressure.

In one embodiment, excess alcohol of general formula (IV), (V) or (VI) is being distilled off, right after addition of the catalyst.

In another embodiment, at the end of the synthesis, unreacted alcohol of the general formula (IV), (V) or (VI) will be removed, e.g., by distilling it off. Such removal can be started after neutralization of the acidic catalyst with, e.g., a base such as sodium hydroxide or MgO. The temperature for distilling off the excess alcohol is selected in accordance with the alcohol of general formula (II). In many cases, a temperature in the range of from 140 to 215° C. is selected, and a pressure in the range of from 1 mbar to 500 mbar.

In one embodiment, the process according to the invention additionally comprises one or more purification steps. Possible purification steps can be selected from bleaching, e.g., with a peroxide such as hydrogen peroxide, filtering over s adsorbent such as silica gel, and treatment with charcoal.

A further aspect of is a process for making mixtures according to the invention, in brief also being referred to as mixing process according to the invention. The mixing process according to the invention can be carried out by mixing at least one mixture according to the invention with at least one surfactant that is not covered by either of formulae (I) to (III), preferably with at least one non-ionic surfactant that is not covered by either of formulae (I) to (III). Particularly preferred further surfactants are selected from alkyl polyglycosides based on linear fatty alcohols, for example linear $C_8$-$C_{14}$-alkanols, in bulk or as preferably as aqueous formulation.

The mixing process according to the invention can be carried out by mixing at least one mixture according to the invention at room temperature or at elevated temperature, for example at temperatures in the range of from 25 to 60° C., in bulk or as aqueous formulation. Aqueous formulations can be selected from aqueous dispersions and aqueous solutions, aqueous solutions being preferred. Preferably, mixing is carried out by combining at least one aqueous formulation comprising a mixture according to the invention and at least one surfactant that is not covered by either of formulae (I) to (III), preferably at least one non-ionic surfactant that is not covered by either of formulae (I) to (III). Particularly preferred are alkyl polyglycosides based on linear fatty alcohols, for example linear $C_8$-$C_{14}$-alkanols.

In one embodiment of the present invention, the mixing process according to the invention is being carried out by mixing an aqueous solution comprising in the range of from 40 to 60% by weight of mixture according to the invention and at least one surfactant that is not covered by either of formulae (I) to (III), at a temperature in the range of from 10 to 80° C., preferably 20 to 60° C.

A further aspect of the present invention is the use of mixtures according to the invention or mixtures according to the invention for cleaning hard surfaces. A further aspect of the present invention is a process for cleaning hard surfaces by using a mixture according to the invention, said process also being referred to as cleaning process according to the present invention or inventive cleaning process. The cleaning process according to the present invention includes applying a mixture according to the invention to such a hard surface. In order to perform the cleaning process according to the present invention, it is possible to use any mixture according to the invention as such or—preferably—as aqueous formulation. In such aqueous formulations, it is preferred that they contain in the range of from 35 to 80% by weight of at least one mixture according to the invention.

Hard surfaces as used in the context with the present invention are defined as surfaces of water-insoluble and—preferably—non-swellable materials. In addition, hard surfaces as used in the context of the present invention are insoluble in acetone, white spirit (mineral turpentine), and ethyl alcohol. Hard surfaces as used in the context of the present invention preferably also exhibit resistance against manual destruction such as scratching with fingernails. Preferably, they have a Mohs hardness of 3 or more. Examples of hard surfaces are glassware, tiles, stone, china, enamel, concrete, leather, steel, other metals such as iron or aluminum, furthermore wood, plastic, in particular melamine resins, polyethylene, polypropylene, PMMA, polycarbonates, polyesters such as PET, furthermore polystyrene and PVC, and furthermore, silicon (wafers) surfaces. Particularly advantageous are inventive formulations when used for cleaning hard surfaces that are at least part of structured objects. In the context, such structured objects refer to objects having, e. g. convex or concave elements, notches, furrows, corners, or elevations like bumps.

Fibers as used in the context with the present invention can be of synthetic or natural origin. Examples of fibers of natural origin are cotton and wool. Examples of fibers of synthetic origin are polyurethane fibers such as Spandex® or Lycra®, polyester fibers, polyamide fibers, and glass wool. Other examples are biopolymer fibers such as viscose, and technical fibers such as GoreTex®. Fibers may be single fibers or parts of textiles such as knitware, wovens, or nonwovens.

In order to perform the inventive cleaning process inventive formulations are being applied. Preferably, inventive formulations are applied in their embodiments as aqueous formulations, comprising, e. g., 10 to 99.9% by weight water. Inventive formulations can be dispersions, solutions, gels, or solid blocks, emulsions including microemulsions, and foams, preferred are solutions. They can be used in highly diluted form, such as 1:10 up to 1:50.

In order to perform the inventive cleaning process, any hard surface or fiber or arrangement of fibers can be contacted (brought into contact) with an inventive formulation.

When contacting hard surfaces with inventive formulations, inventive formulations can be applied at ambient temperature. In a further embodiment, inventive formulations can be used at elevated temperatures, such as 30 to 85° C., for examples by using an inventive formulation that has a temperature of 30 to 85° C., or by applying an inventive formulation to a preheated hard surface, e. g., preheated to 30 to 85° C.

In one embodiment, it is possible to apply an inventive formulation to a hard surface under normal pressure. In a further embodiment, it is possible to apply inventive formulation to a hard surface under pressure, e. g., by use of a high-pressure cleaner or a pressure washer.

In one embodiment of the present invention, application duration of inventive formulation can be in the range of from one second up to 24 hours, preferably in the range of 30 min to 5 hours in the case of fiber cleaning and preferably one second up to 1 hour in cases such as floor cleaning, kitchen cleaning or bathroom cleaning.

Hard surface cleaning in the context of the present invention can include removing heavy soiling, removing slight soiling and removing dust, even removing small quantities of dust.

Examples of soiling to be removed are not limited to dust and soil but can be soot, hydrocarbons, e.g., oil, engine oil, furthermore residues from food, drinks, body fluids such as blood or excrements, furthermore complex natural mixtures such as grease, and complex synthetic mixtures such as paints, coatings, and pigment containing grease.

The contacting of the hard surface with inventive formulation can be performed once or repeatedly, for example twice or three times.

After having performed the contacting the hard surface with inventive formulation the remaining inventive formulation containing soil or dust will be removed. Such removal can be effected by removal of the object with the now clean hard surface from the respective inventive formulation or vice versa, and it can be supported by one or more rinsing step(s).

After having performed the inventive cleaning process, the object with the now-clean hard surface can be dried. Drying can be effected at room temperature or at elevated temperature such as, e.g., 35 to 95° C. Drying can be performed in a drying oven, in a tumbler (especially with fibers and with fabrics), or in a stream of air having room temperature or elevated temperature such as 35 to 95° C. Freeze-drying is another option.

By performing the inventive cleaning process, hard surfaces can be cleaned very well. In particular, objects with structured hard surfaces can be cleaned well.

In one embodiment of the present invention, formulations according to the present invention can contain further organic or inorganic materials.

In one embodiment of the present invention, aqueous formulations according to the present invention may further contain at least one by-product, stemming from the synthesis of cornpound of general formulae (I), (II) or (III).

Such by-products can be, for example, starting materials from the syntheses of compounds according to general formulae (I), (II) or (III) such as the alcohols of (IV), (V) or (VI). Examples of further by-products from the syntheses of compounds according to general formulae (I), (II) and (III) are polycondensation products of monosaccharides $G^1$.

Formulations according to the present invention can be solid, liquid or in the form of slurries. Preferably, formulations according to the present invention are selected from liquid and solid formulations. In one embodiment, formulations according to the present invention are aqueous, preferably liquid aqueous formulations.

In one embodiment of the present invention, formulations according to the present invention can contain 0.1 to 90% by weight of water, based on total of the respective formulation.

In one embodiment of the present invention, formulations according to the invention have a pH value in the range of from zero to 14, preferably from 3 to 11. The pH value can be chosen according to the type of hard surface and the specific application. It is, e.g., preferred to select a pH value in the range of from 3 to 4 for bathroom or toilet cleaners. It is furthermore preferred to select a pH value in the range of from 4 to 10 for dishwashing or floor cleaners.

In one embodiment of the present invention, inventive formulations contain at least one active ingredient. Active ingredients can be selected from soaps, anionic surfactants, such as LAS (linear alkylbenzenesulfonate) or paraffine sulfonates or FAS (fatty alcohol sulfates) or FAES (fatty alcohol ether sulfates), furthermore acids, such as phosphoric acid, amidosulfonic acid, citric acid, lactic acid, acetic acid, other organic and inorganic acids, furthermore organic solvents, such as butyl glycol, n-butoxypropanol, especially 1-butoxy-2-propanol, ethylene glycol, propylene glycol, glycerine, ethanol, monoethanolamine, and isopropanol.

In one embodiment of the present invention, inventive formulations comprise at least one organic acid, selected from acetic acid, citric acid, and methanesulfonic acid.

In one embodiment of the present invention, inventive formulations contain at least one or more active ingredients selected from non-ionic surfactants which are different from compounds of formulae (I), (II) and (III). Examples of suitable non-ionic surfactants are alkoxylated n-$C_{12}$-$C_{20}$-fatty alcohols, such as n-$C_{10}$-$C_{20}$-alkyl(EO)$_m$OH with m being in the range of from 5 to 100, furthermore block copolymers of ethylene oxide and propylene oxide, such as poly-EO-poly-PO-poly-EO with $M_w$ in the range of from 3,000 to 5,000 g/mol PO content of from 20 to 50% by mass, furthermore alkyl polyglycosides, preferably branched $C_8$-$C_{10}$-alkyl polyglucosides, especially $C_8$-$C_{10}$-alkyl polyglucosides with a branching in 2-position of the respective $C_8$-$C_{10}$-alkyl group.

In one embodiment of the present invention, inventive formulations can be used as bath cleaners, as sanitary cleaners, as kitchen cleaners, as toilet cleaners, as toilet bowl cleaners, as sanitary descalers, as all-purpose household cleaners, as all-purpose household cleaner concentrates, as metal degreasers, as all purpose-household spray cleaners, as hand dish cleaners, as automatic dishwashing agents, or floor cleaners, as hand cleaners.

In one embodiment of the present invention, inventive formulations can contain at least one biocide or preservative, such as benzalkonium chlorides.

In another embodiment of the present invention, inventive formulations can be used as laundry detergents.

In one embodiment of the present invention, inventive formulations can contain one or more active ingredients selected from inorganic builders such as phosphates, such as triphosphates.

Phosphate-free formulations according to the present invention are preferred. In the context of the present invention, the term "phosphate-free" refers to formulations with 0.5% by weight of phosphate maximum, based on the total solids content and measured by gravimetric methods, and phosphate-free formulations can contain a minimum of 50 ppm (weight) phosphate or less.

Examples of preferred inorganic builders are silicates, silicates, carbonates, and alumosilicates. Silicates and alumosilicates can be selected from crystalline and amorphous materials.

In one embodiment of the present invention, inorganic builders are selected from crystalline alumosilicates with ion-exchanging properties, such as, in particular, zeolites. Various types of zeolites are suitable, in particular zeolites A, X, B, P, MAP and HS in their Na form or in forms in which Na is partially replaced by cations such as $Li^+$, $K^+$, $Ca^{2+}$, $Mg^{2+}$ or ammonium.

Suitable crystalline silicates are, for example, disilicates and sheet silicates. Crystalline silicates can be used in the form of their alkali metal, alkaline earth metal or ammonium salts, preferably as Na, Li and Mg silicates.

Amorphous silicates, such as, for example, sodium metasilicate, which has a polymeric structure, or Britesil® H2O (manufacturer: Akzo) can be selected.

Suitable inorganic builders based on carbonate are carbonates and hydrogencarbonates. Carbonates and hydrogencarbonates can be used in the form of their alkali metal, alkaline earth metal or ammonium salts. Preferably, Na, Li and Mg carbonates or hydrogencarbonates, in particular sodium carbonate and/or sodium hydrogencarbonate, can be selected. Other suitable inorganic builders are sodium sulphate and sodium citrate.

In one embodiment of the present invention, inventive formulations can contain at least one organic complexing agent (organic cobuilders) such as EDTA (N,N,N',N'-ethylenediaminetetraacetic acid), NTA (N,N,N-nitrilotriacetic acid), MGDA (2-methylglycine-N,N-diacetic acid), GLDA (glutamic acid N,N-diacetic acid), and phosphonates such as 2-phosphono-1,2,4-butanetricarboxylic acid, aminotri (methylenephosphonic acid), 1-hydroxyethylene(1,1-diphosphonic acid) (HEDP), ethylenediaminetetramethylenephosphonic acid, hexamethylenediaminetetramethylenephosphonic acid and diethylenetriaminepentamethylenephosphonic acid and in each case the respective alkali metal salts, especially the respective sodium salts. Preferred are the sodium salts of HEDP, of GLDA and of MGDA.

In one embodiment of the present invention, inventive formulations can contain one or more active ingredients selected from organic polymers, such as polyacrylates and copolymers of maleic acid-acrylic acid.

In one embodiment of the present invention, inventive formulations can contain one or more active ingredients selected from alkali donors, such as hydroxides, silicates, carbonates.

In one embodiment of the present invention, inventive formulations can contain one or more further ingredients such as perfume oils, oxidizing agents and bleaching agents, such as perborates, peracids or trichloroisocyanuric acid, Na or K dichloroisocyanurates, and enzymes.

Most preferred enzymes include lipases, amylases, cellulases and proteases. In addition, it is also possible, for example, to use esterases, pectinases, lactases and/or peroxidases.

Enzyme(s) may be deposited on a carrier substance or be encapsulated in order to protect them from premature decomposition.

In one embodiment of the present invention, inventive formulations can contain one or more active ingredients such as graying inhibitors and soil release polymers. Examples of suitable soil release polymers and/or graying inhibitors are:

Polyesters of polyethylene oxides and ethylene glycol and/or propylene glycol as diol component(s) with aromatic dicarboxylic acids or combinations of aromatic and aliphatic dicarboxylic acids as acid component(s), polyesters of aromatic dicarboxylic acids or combinations of aromatic and aliphatic dicarboxylic acids as acid component(s) with di- or polyhydric aliphatic alcohols as diol component(s), in particular with polyethylene oxide, said polyesters being capped with polyethoxylated $C_1$-$C_{10}$-alkanols.

Further examples of suitable soil release polymers are amphiphilic copolymers, especially graft copolymers of vinyl esters and/or acrylic esters onto polyalkylene oxides. Further examples are modified celluloses such as, for example, methylcellulose, hydroxypropylcellulose and carboxymethylcellulose.

In one embodiment of the present invention, inventive formulations can contain one or more active ingredients selected from dye transfer inhibitors, for example homopolymers and copolymers of vinylpyrrolidone, of vinylimidazole, of vinyloxazolidone or of 4-vinylpyridine N-oxide, each having average molar masses $M_w$ of from 15,000 to 100,000 g/mol, and cross-linked finely divided polymers based on the above monomers.

In one embodiment of the present invention, inventive formulations contain 0.05 to 50% by weight, preferably 1 to 20% by weight organic complexing agent, based on the total solids content of the respective inventive formulation.

In one embodiment of the present invention, inventive formulations contain 0.1 to 80% by weight, preferably 5 to 55% by weight anionic surfactant, based on the total solids content of the respective inventive formulation.

In one embodiment of the present invention, inventive formulations can contain one or more active ingredients selected from defoamers. Examples of suitable defoamers are silicon oils, especially dimethyl polysiloxanes which are liquid at room temperature, without or with silica particles, furthermore microcrystalline waxes and glycerides of fatty acids.

In one embodiment of the present invention, inventive formulations do not contain any defoamer which shall mean in the context of the present invention that said inventive formulations comprise less than 0.1% by weight of silicon oils and less than 0.1% by weight of glycerides of fatty acids and less than 0.1% by weight of microcrystalline waxes, referring to the total solids content of the respective inventive formulation. In the extreme, inventive formulations do not contain any measureable amounts of silicon oils or glycerides of fatty acids at all.

A further aspect of the present invention refers to mixtures of alcohols, comprising in the range of from 93 to 97% by weight alcohol of general formula (IV),

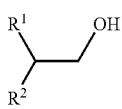
(IV)

in the range of from 3 to 6.5% by weight alcohol of general formula (V)

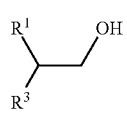
(V)

and in the range of from 0.1 to 0.5% by weight alcohol of general formula (VI)

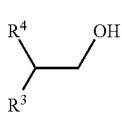
(VI)

wherein the integers are defined as follows:
$R^1$ is $-(CH_2)_nCH_3$,
$R^2$ is $-(CH_2)_{n+2}CH_3$,
$R^3$ is $-(CH_2)_{n+1}CH(CH_3)_2$,
$R^4$ is $-(CH_2)_{n-1}CH(CH_3)_2$
n is a number in the range of from 1 to 4, preferred is 1 or 2, and particularly preferred is 2.

Said mixtures are also being referred to as inventive mixtures. Inventive mixtures are ell suited for making the inventive mixtures of compounds. Inventive mixtures can be made, for example, by a Guerbet reaction of appropriate mixtures of $R^1CH_2CH_2OH$ and $R^4CH_2CH_2OH$.

WORKING EXAMPLES

General Remarks

Percentages are % by weight (wt %) unless expressly noted otherwise.

All measurements with respect to colour number were performed on a 10% by volume diluted paste or solution, respectively. For dilution, a 15% by volume aqueous solution of isopropanol was used.

The lab plant for producing compounds according to the invention consisted of a jacketed 4 l glass reactor, a condenser with a Dean-Stark trap, a three stage agitator, a distillation receiver and a dropping funnel. The pressure was set with a vacuum system consisting of a vacuum pump, a pressure indicator, a pressure controller and two cold traps cooled with liquid nitrogen. To remove the excess alcohol by distillation, a 2 l round flask equipped with a stirrer, a PT 100, a Claisen distillation head, a cooler, a distillate receiver, a pressure measurement and a vacuum pump were used.

I. Synthesis of Compounds According to the Invention

As alcohol for the synthesis, the following inventive mixture of alcohols was sued:
95.47% by weight (IV.1),
4.13% by weight (V.1) and
0.18% by weight (VI.1)
Experimental error: ±0.02%

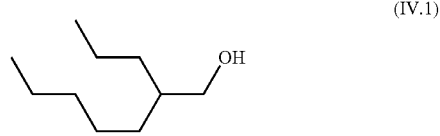
(IV.1)

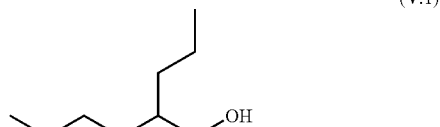
(V.1)

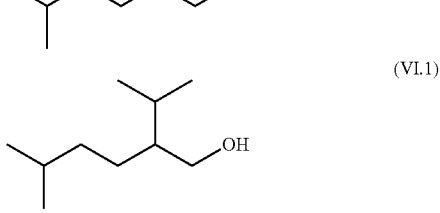
(VI.1)

It was obtained by a Guerbet reaction of a mixture of n-pentanol with iso-amyl alcohol.

The inventive mixture was thus a mixture of isomers hereinafter also being referred to as "alcohol mixture (IV.1) to (VI.1)".

I.1 Synthesis of Inventive Mixture of Compounds (I.1), (II.1) and (III.1)

The 4 l glass reactor of the lab plant described above was charged with 666.8 g (3.36 moles) of glucose monohydrate and 1812.6 g of alcohol mixture (IV.1) to (VI.1). The resultant slurry was dried at 75° C. at a pressure of 30 mbar for a period of 90 minutes under stirring. Then, the pressure was adjusted to ambient pressure, and the slurry was heated to 90° C. An amount of 5.7 g of sulfosuccinic acid (70% by weight), dissolved in 200 g of the above specified alcohol mixture (IV.1) to (VI.1), was added and heating was continued until a temperature of 110° C. was reached. The pressure was set to 30 mbar, and, under stirring, the water formed was distilled off at the Dean-Stark trap equipped with cold traps. After 5.5 hours, no more water was formed, and the amount of water to be formed theoretically was in the cold traps.

The reaction was then quenched by neutralizing the catalyst with 2.43 g of 50% by weight aqueous NaOH. The pH value, measured in a 10% solution in isopropanol/water (1:10), was at least 10.2. The reaction mixture was then transferred into a round flask, excess alcohol mixture (IV.1)

to (VI.1) was distilled off at 140° C./1 mbar. During the removal of the excess alcohol mixture (IV.1) to (VI.1), the temperature was step-wise raised to 180° C. within 2.75 hours. When no more alcohol would distil off, the liquid reaction mixture was stirred into water (room temperature) in order to adjust the solids content to 60% and cooled to ambient temperature, hereby forming an aqueous paste. The inventive mixture of compounds (I.1), (II.1) and (III.1) so obtained had an average degree of polymerization (number average) of 1.38 and a residual alcohol content of 0.04 g, and the paste so obtained had a water content of 38.4%. The pH value was 9.0, the colour number (Gardner) was 8.1.

In order to improve the colour, 927 g of the above aqueous paste were transferred into a 4 l vessel and reacted with 73.5 g of 35% by weight aqueous $H_2O_2$ which was added in a way that the total peroxide content was in the range of from 300 to 1,500 ppm, determined with Merckoquant peroxide test sticks. The pH value was maintained in the range from 10.0 to 10.8 Finally, the pH value was adjusted to 11.5 with 50% by weight aqueous NaOH. The colour number (Gardner) had dropped to 3.0, and the water content had raised to 40.0%. All measurements with respect to pH value and peroxide content were performed on a 10% by volume diluted paste. For dilution, a 15% by volume aqueous solution of isopropanol was used.

I.2 Synthesis of Inventive Mixture of Compounds (I.2), (II.2) and (III.2)

The 4 l glass reactor described above was charged with 464.0 g (3.09 moles) of xylose and 1713.8 g of alcohol mixture (IV.1) to (VI.1). The resultant slurry heated to 50° C. An amount of 1.0 g of sulfosuccinic acid (70% by weight), dissolved in 150 g of the above specified alcohol mixture (IV.1) to (VI.1), was added and heating was continued until a temperature of 95° C. was reached. The pressure was set to 30 mbar, and, under stirring, the water formed was distilled off at the Dean-Stark trap equipped with cold traps. After 600 minutes, no more water was formed, and the amount of water to be formed theoretically was in the cold traps.

The reaction was then quenched by neutralizing the catalyst with 1.2 g of 50% by weight aqueous NaOH. The pH value, measured in a 10% solution in isopropanol/water (1:10), was at least 11.0. The reaction mixture was then transferred into a round flask, and at 140° C./1 mbar, excess alcohol mixture (IV.1) to (VI.1) was distilled off. During the removal of the excess alcohol mixture (IV.1) to (VI.1), the temperature was step-wise raised to 175° C. within 2 hours. When no more alcohol would distil off, the liquid reaction mixture was stirred into water (room temperature) in order to adjust the solids content to 60% and cooled to ambient temperature, hereby forming an aqueous paste. The inventive mixture of compounds (I.2), (II.2) and (III.2) had an average degree of polymerization (number average) of 1.2 and a residual alcohol content of 0.2 g, and the paste so obtained had a water content of 39.9%. The pH value was 6.4, the colour number (Gardner) was >10.

In order to improve the colour, 1040 g of the above paste were transferred into a 4 l vessel and reacted with 36.0 g of 35% by weight aqueous $H_2O_2$ which was added over a time of 3 h into the reactor. The pH value was maintained in the range from 10.1 to 11.2. Finally, the pH value was adjusted to 11.5 with 50% by weight aqueous NaOH. The colour number (Gardner) had dropped to 2.5, and the water content had raised to 41.9%. All measurements with respect to pH value and peroxide content were performed on a 10% by volume diluted paste. For dilution, a 15% by volume aqueous solution of isopropanol was used.

I.3 Synthesis of Comparative Compound (1.1)

Pure alcohol (IV.1) was obtained from an alcohol mixture (IV.1) to (VI.1) by fractionate distillation at 50 mbar with a packed column. Alcohol mixtures of (IV.1) to (VI.1) can be characterized by gas chromatography, for example operated with a 30 m Optima-1 column, diameter: 0.32 mm, FD 0.5μ, heating protocol: oven at 50° C. for 2 minutes, then heating with a rate of 20° C./min until a temperature of 130° C. has been reached, maintaining at 130° C. for 5 min., then heating with a rate of 7.5° C./min until a temperature of 200° C. has been reached, then increase heating rate to 20°/min until 250° C. have been reached, maintain at 250° C. until a total time of 40 min.

The synthesis of protocol I.1 was repeated but alcohol mixture (IV.1) to (VI.1) was replaced by 1,301 g of alcohol (IV.1). Comparative compound C-(I.1) was obtained.

I.4 Synthesis of Comparative Compound (I.2)

The synthesis of protocol 1.2 was repeated but alcohol mixture (IV.1) to (VI.1) was replaced by 1250 g of alcohol (IV.1). Comparative compound C-(I.2) was obtained.

II. Application Tests

In the application tests, inventive mixture of compounds (I.1), (II.1) and (III.1) will also be abbreviated as (M.1), and inventive mixture of compounds (I.2), (II.2) and (III.2) will also be abbreviated as (M.2).

II.1 Foaming Power

The foaming power was determined according to EN12728/DIN 53902 at 40° C. with water of 10° dH (German hardness). As laundry cleaners ("LCF"), aqueous solutions consisting of 2 g/l of respective surfactant (±0.02 g) in distilled water were applied. The temperature was kept constant in a range of ±2° C.

The results are summarized in table 1.

TABLE 1

| Wetting power | |
|---|---|
| surfactant | Wetting power at 40° C. [s] |
| (M.1) | 140 |
| C-(I.1) | 410 |
| (M.2) | 40 |
| C-(M.2) | 60 |

It can be seen that the polyglucoside based on alcohol mixture (IV.1) to (VI.1) is superior over polyglucoside based on 2-n-propylheptanol with respect to the wetting power, and that the polyxyloside based on alcohol mixture (IV.1) to (VI.1) is superior the respective polyxyloside based on 2-n-propylheptanol. Polyxylosides, however, have a higher price than polyglucosides and are therefore not accepted in all applications.

II.2 Foam Stability Tests

The experiments for determination of the foam stability were carried out in a Sita Foam Tester R-2000. As test solutions, aqueous solutions of 1 g/l of the respective polyglycoside in distilled water were used. An amount of 300 ml of the respective test solution was pumped into a glass vessel and heated to the respective temperature. Then it was stirred for 1 minute at 1,500 rpm. Then the volume of the foam was determined. Stirring and measuring was repeated 9 times. The stirrer was then set off, and the decay of the foam was determined. Measurements 10 minutes after set-off are listed in Table 2 or 2a or 2b or 2c, respectively. The results are summarized in Table 3. For Table 2a, the experiments were repeated but water with 16° dH (German hardness) was used instead of distilled water. For Table 2b, the experiments were repeated but a 1% by weight aqueous NaOH solution was used instead of distilled water. For Table 2c, the experiments were repeated but a 1% by weight aqueous methylsulfonic acid solution was used instead of distilled water.

TABLE 2

Results of the foam stability tests in distilled water

| Surfactant | Temperature [° C.] | Maximum foam volume [ml] | Reached after time [min] | Foam volume 10 minutes after stirrer set-off [ml] |
|---|---|---|---|---|
| (M.1) | 20 | 897 | 10 | 543 |
| C-(I.1) | 20 | 911 | 3 | 874 |
| (M.2) | 20 | 426 | 10 | 327 |
| C-(I.2) | 20 | 927 | 4 | 871 |
| (M.1) | 40 | 939 | 6 | 591 |
| C-(I.1) | 40 | 989 | 5 | 936 |
| (M.2) | 40 | 471 | 10 | 155 |
| C-(I.2) | 40 | 1014 | 5 | 693 |
| (M.1) | 60 | 1041 | 8 | 27 |
| C-(I.1) | 60 | 1099 | 6 | 640 |
| (M.2) | 60 | 587 | 10 | 11 |
| C-(I.2) | 60 | 1077 | 6 | 147 |

TABLE 2a

Results of the foam stability tests in water of 16°dH

| Surfactant | Temperature [° C.] | Maximum foam volume [ml] | Reached after time [min] | Foam volume 10 minutes after stirrer set-off [ml] |
|---|---|---|---|---|
| (M.1) | 20 | 268 | 8 | 21 |
| C-(I.1) | 20 | 921 | 10 | 878 |
| (M.2) | 20 | 45 | 7 | 20 |
| C-(I.2) | 20 | 228 | 10 | 184 |
| (M.1) | 40 | 858 | 10 | 0 |
| C-(I.1) | 40 | 976 | 6 | 851 |
| (M.2) | 40 | 72 | 1 | 0 |
| C-(I.2) | 40 | 262 | 10 | 8 |
| (M.1) | 60 | 680 | 10 | 0 |
| C-(I.1) | 60 | 990 | 6 | 129 |
| (M.2) | 60 | 108 | 2 | 0 |
| C-(I.2) | 60 | 363 | 10 | 0 |

TABLE 2b

Results of the foam stability tests in 1 wt % aqueous NaOH

| Surfactant | Temperature [° C.] | Maximum foam volume [ml] | Reached after time [min] | Foam volume 10 minutes after stirrer set-off [ml] |
|---|---|---|---|---|
| (M.1) | 20 | 433 | 10 | 0 |
| C-(I.1) | 20 | 730 | 10 | 163 |
| (M.1) | 40 | 711 | 10 | 0 |
| C-(I.1) | 40 | 869 | 10 | 61 |
| (M.1) | 60 | 589 | 10 | 0 |
| C-(I.1) | 60 | 668 | 10 | 6 |

TABLE 2c

Results of the foam stability tests in 1 wt % aqueous methylsulfonic acid

| Surfactant | Temperature [° C.] | Maximum foam volume [ml] | Reached after time [min] | Foam volume 10 minutes after stirrer set-off [ml] |
|---|---|---|---|---|
| C-(I.1) | 20 | 354 | 10 | 298 |
| (M.2) | 20 | 13 | 9 | 0 |

TABLE 2c-continued

Results of the foam stability tests in 1 wt % aqueous methylsulfonic acid

| Surfactant | Temperature [° C.] | Maximum foam volume [ml] | Reached after time [min] | Foam volume 10 minutes after stirrer set-off [ml] |
|---|---|---|---|---|
| C-(I.2) | 20 | 39 | 4 | 0 |
| C-(I.1) | 40 | 1045 | 10 | 17 |
| (M.2) | 40 | 13 | 4 | 0 |
| C-(I.2) | 40 | 60 | 10 | 0 |
| C-(I.1) | 60 | 899 | 10 | 0 |
| (M.2) | 60 | 0 | 0 | 0 |
| C-(I.2) | 60 | 111 | 8 | 0 |

II.3 Emulsifying Behaviour

General Method:

In a 400-ml-beaker, 50 g of a 2% by weight of aqueous solution (in distilled water) of the respective surfactant were mixed with 50 g of olive oil at 23° C. The mixture was stirred with 1200 (±3) rpm for exactly 2 minutes with the help of a power mixer, the mixer being positioned in the phase boundary oil-water. The emulsion so produced was then transferred to a cylinder to be observed. The emulsion stability was determined visually by measuring the volume of the water phase after one (1) and four (4) hours. The less "oil-free" water phase the more stable the emulsion. Results are summarized in Table 3.

TABLE 3

Emulsifying behaviour

| surfactant | Water phase after 1 h [ml] | Water phase after 4 h [ml] |
|---|---|---|
| (M.1) | 4 | 14 |
| C-(I.1) | 8 | 23 |

With (M.2) vs. C-(I.2), a similar trend can be observed.

The invention claimed is:

1. Mixture of compounds, comprising
    (A) in the range of from 93 to 97% by weight compound of general formula (I),

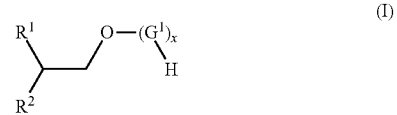

(I)

(B) in the range of from 3 to 6.5% by weight compound of general formula (II),

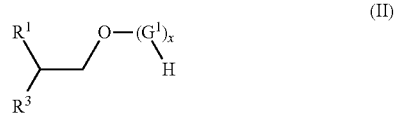

(II)

(C) and in the range of from 0.1 to 0.5% by weight compound of general formula (III)

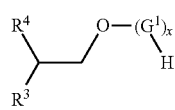

(III)

wherein the integers are defined as follows:
$R^1$ is $-(CH_2)_nCH_3$,
$R^2$ is $-(CH_2)_{n+2}CH_3$,
$R^3$ is $-(CH_2)_{n+1}CH(CH_3)_2$,
$R^4$ is $-(CH_2)_{n-1}CH(CH_3)_2$
$G^1$ is selected from monosaccharides with 4 to 6 carbon atoms,
x in the range of from 1.1 to 10,
n is a number in the range of from 1 to 4.

2. Mixture of compounds according to claim 1, characterized in that $G^1$ is selected from glucose, arabinose and xylose.

3. Mixture of compounds according to claim 1, characterized in that x is in the range of from 1.15 to 2.

4. Mixture of compounds according to claim 1, characterized in that n is 1.

5. Mixture of compounds according to claim 1, characterized in that in molecules with x being 2 or more, the saccharide groups are linked in 1,4-position(s).

6. Mixture, containing at least one mixture according to claim 1 and at least one further isomer being different from each of compound according to general formulae (I), compound (II) and (III).

7. Process for making a mixture of compounds according to claim 1, comprising the step of reacting a mixture of alcohols of the general formulae (IV), (V) and (VI)

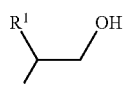

(IV)

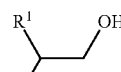

(V)

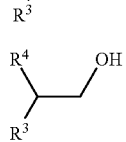

(VI)

with a monosaccharide, disaccharide or polysaccharide containing a $G^1$ group in the presence of a catalyst.

8. Process for cleaning hard surfaces comprising contacting said hard surface with a mixture of compounds according to claim 1.

9. Process according to claim 8, characterized in that the cleaning comprises a degreasing.

10. Aqueous formulation, containing in the range of from 0.05 to 50% by weight of at least one mixture of compounds according to claim 1.

11. Aqueous formulation according to claim 10, characterized that it further contains at least one by-product or starting material, stemming from the syntheses of compounds according to general formulae (I), (II) and (III).

12. Mixture of alcohols, comprising
in the range of from 93 to 97% by weight alcohol of general formula (IV),

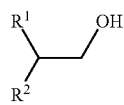

(IV)

in the range of from 3 to 6.5% by weight alcohol of general formula (V)

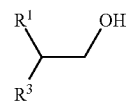

(V)

and in the range of from 0.1 to 0.5% by weight alcohol of general formula (VI)

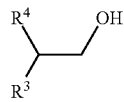

(VI)

wherein the integers are defined as follows:
$R^1$ is $-(CH_2)_nCH_3$,
$R^2$ is $-(CH_2)_{n+2}CH_3$,
$R^3$ is $-(CH_2)_{n+1}CH(CH_3)_2$,
$R^4$ is $-(CH_2)_{n-1}CH(CH_3)_2$
n is a number in the range of from 1 to 4.

* * * * *